(12) United States Patent
Wei et al.

(10) Patent No.: US 9,133,130 B2
(45) Date of Patent: Sep. 15, 2015

(54) N-TYPE DOPED ORGANIC MATERIALS AND METHODS THEREFOR

(75) Inventors: Peng Wei, Stanford, CA (US); Zhenan Bao, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 650 days.

(21) Appl. No.: 13/080,564

(22) Filed: Apr. 5, 2011

(65) Prior Publication Data

US 2011/0240980 A1 Oct. 6, 2011

Related U.S. Application Data

(60) Provisional application No. 61/321,033, filed on Apr. 5, 2010.

(51) Int. Cl.
*H01L 51/00* (2006.01)
*H01L 51/05* (2006.01)
(Continued)

(52) U.S. Cl.
CPC .............. *C07D 235/18* (2013.01); *B82Y 10/00* (2013.01); *B82Y 30/00* (2013.01); *C07D 409/04* (2013.01); *C07D 409/14* (2013.01); *H01L 51/005* (2013.01); *H01L 51/0047* (2013.01); *H01L 51/0048* (2013.01); *H01L 51/0545* (2013.01); *H01L 51/5296* (2013.01); *H01L 51/0533* (2013.01); *H01L 51/0566* (2013.01); *Y02E 10/549* (2013.01)

(58) Field of Classification Search
CPC ............ H01L 51/0047; H01L 51/0048; H01L 51/0533; H01L 51/5296; H01L 51/0545

USPC ........................................................ 257/40
See application file for complete search history.

(56) References Cited

U.S. PATENT DOCUMENTS

2004/0234809 A1* 11/2004 Chen et al. .................... 428/690
2006/0284253 A1* 12/2006 Han et al. ...................... 257/347
(Continued)

FOREIGN PATENT DOCUMENTS

DE       WO2009/000237 A1 * 12/2008
EP       2 246 862 A1 *  3/2010
WO       2009000237 A1   12/2008

OTHER PUBLICATIONS

Nollau, A., Pfeiffer, M., Fritz, T. & Leo, K., "Controlled n-Type Doping of a Molecular Organic Semiconductor: Naphthalenetetracarboxylic dianhydride (NTCDA) Doped with bis(ethylenedithio)-tetrathiafulvalene (BEDT-TTF)." J. Appl. Phys. vol. 87, pp. 4340-4343, (2000).

(Continued)

*Primary Examiner* — Phat X Cao
(74) *Attorney, Agent, or Firm* — Crawford Maunu PLLC (57) ABSTRACT

In accordance with various embodiments, an organic electronic device includes an n-type dopant material including an imidazole-based material having a hydrogen-based material bonded between nitrogen atoms. The n-type dopant material n-dopes an organic material, and can be used to mitigate degradation in mobility due to conditions such as exposure to ambient atmosphere, which can effect an undesirable reduction in charge transport. Other embodiments are directed to carbon nanotubes or graphene structures with this type of n-type dopant, wherein the Fermi level for the carbon nanotubes or graphene structures is below −2.5 eV to effect such n-type doping.

30 Claims, 7 Drawing Sheets

(51) Int. Cl.
| | |
|---|---|
| H01L 51/52 | (2006.01) |
| C07D 235/18 | (2006.01) |
| B82Y 10/00 | (2011.01) |
| B82Y 30/00 | (2011.01) |
| C07D 409/04 | (2006.01) |
| C07D 409/14 | (2006.01) |

(56) References Cited

U.S. PATENT DOCUMENTS

| | | | |
|---|---|---|---|
| 2007/0018154 A1 | 1/2007 | Bae et al. | |
| 2008/0283826 A1 | 11/2008 | Zheng et al. | |
| 2010/0127241 A1* | 5/2010 | Gruner et al. | 257/20 |
| 2010/0187515 A1 | 7/2010 | Limmert et al. | |
| 2010/0301277 A1* | 12/2010 | Hartmann et al. | 252/500 |
| 2011/0248267 A1 | 10/2011 | Wei et al. | |
| 2012/0018706 A1* | 1/2012 | Kagan et al. | 257/40 |

OTHER PUBLICATIONS

Maennig, B.; Pfeiffer, M.; Nollau, A.; Zhou, X.; Leo, K. And Simon, P., "Controlled p-Type Doping of Polycrystalline and Amorphous Organic Layers: Self-consistent Description of Conductivity and Field-effect Mobility by a Microscopic Percolation Model." Phys. Rev. B, 64, No. 195208, (2001).
Gao, W. and Kahn, A., "Controlled p-doping of Zinc Phthalocyanine by Coevaporation with Tetrafluorotetracyanoquinodimethane: A Direct and Inverse Photoemission Study." Appl. Phys. Lett., vol. 79, pp. 4040, (2001).
Werner, A. G.; Li, F.; Harada, K.; Pfeiffer, M.; Fritz, T. and Leo, K., "Pryonin B as a Donor for n-type Doping of Organic Thin Films." Appl. Phys. Lett., vol. 82, pp. 4495-4497, (2003).
Ouyang, J.; Xu, Q.; Chu, C.-W.; Yang, Y.; Li, G. and Shinar, J., "On the Mechanism of Conductivity Enhancement in poly(3,4-ethylenedioxythiophene):poly(styrene sulfonate) Film Through Solvent Treatment." Polymer, 45, pp. 8843-8450, (2004).
Drechsel, J.; Mannig, B.; Kozlowski, F.; Pfeiffer, M.; Leo, K. and Hoppe, H., "Efficient Organic Solar Cells Based on a Double p-i-n Architecture Using Doped Wide-Gap Transport Layers." Appl. Phys. Lett., 86, No. 244102, (2005).
Singh, T. B. et al., "Fabrication and Characterization of Solution-Processed Methanofullerene-Based Organic Field-Effect Transistors." J. Appl. Phys. 97, 083714, (2005).
Li, F.H., et al., "Acridine Orange Base as a Dopant for n Doping of C60 Thin Films." J. Appl. Phys. 100, 023716, (2006).
Yun, M. et al., "Capacitance-Voltage Characterization of Polyfluorene-Based Metal-Insulator-Semiconductor Diodes." Appl. Phys. Lett. 89, 013506, (2006).
Zhang, X. H.; Domercq, B. & Kippelen, B., "High-performance and Electrically Stable C-60 Organic Field-Effect Transistors." Appl. Phys. Lett., 91, 092114, (2007).
Zhang, X. H. & Kippelen, B., "High-performance C60 n-Channel Organic Field-Effect Transistors Through Optimization of Interfaces." J. Appl. Phys. 104, 104504, (2008).
Chan, C. K.; Zhao, W.;Barlow, S.; Marder, S. and Kahn, A., "Decamethylcobaltocene as an Effieient n-Dopant in Organic Electronic Materials and Devices." Org. Electron., 9, pp. 575-581, (2008).
P. Wöbkenberg et al., "High mobility n-channel organic field-effect transistors based on soluble C60 and C70 fullerence derivative." Synthetic Metals 158, pp. 468-472 (2008).

Chan, C. K.; Zhao, W.; Kahn, A. and Hill, I. G., "Influence of Chemical Doping on the Performance of Organic Photovoltaic Cells." Appl. Phys. Lett., 94, No. 203306, (2009).
Yamagishi, M.; Tominari, Y.; Uemura, T. and Takeya, J., "Air-Stable n-Channel Single-Crystal Transistors with Negligible Threshold Gate Voltage." Appl. Phys. Lett., 94, No. 053305, (2009).
Y. Wang et al., "Supercapacitor Devices Based on Graphene Materials," J. Phys. Chem. 113, pp. 13103-13107 (2009).
K. A. Mkhoyan et al., "Atomic Electronic Structure of Graphene-Oxide," Nato Lett. 9 (3), pp. 1058-1063 (2009).
P. Meduri et al., "Hybrid Tin Oxide Nanowires as Stable and High Capacity Anodes for Li-Ion Batteries," Nano Lett. 9 (2), pp. 612-616 (2009).
Timmreck, R.; Olthof, S.; Leo, K. and Riede, M. K., "Highly Doped Layers as Efficient Electron-Hole Recombination Contacts for Tandem Organic Solar Cells." J. Appl. Phys., 108, No. 033108, (2010).
Meiss, J.; Menke, T.; Leo, K.; Uhrich, C.; Gnehr, W.-M.; Sonntag, S.; Pfeiffer, M. and Riede, M., "Highly Efficient Semitransparent Tandem Organic Solar Cells with Complementary Absorber Materials." Appl. Phys. Lett., 99, No. 043301, (2011).
Meerheim, R.; Olthof, S.; Hermenau, M.; Scholz, S.; Petrich, A.; Tessler, N.; Solomeshch, O.; Lussem, B.; Riede, M. and Leo, K., "Investigation of C60F36 As Low-Volatility P-Dopant in Organic Optoelectronic." J. Appl.Phys., 109, No. 103102, (2001).
Chan et al. "Molecular n-type Doping of 1,4,5,8-naphthalene tetracarboxylic dianhydride by Pyronin B Studied Using Direct and Inverse Photoelectron Spectroscopies," Adv. Funct. Mater. 16, 831-837 (2006). Abstract only.
K. Walzer et al. "Highly efficient organic devices based on electrically doped transport layers." Chem. Rev. 107, 1233-1271 (2007). Abstract/Table of Contents only.
Tanner and J. J. Chen. "On the Mechanism of the Reduction of Alpha-halo Ketones by 1,3-dimethyl-2-phenylbenzimidazoline-reduction by a Set-hydrogen Atom Abstraction Chain Mechanism." J. Org. Chem. 54, 3842-3846 (1989). p. 3842 only.
J. H. Oh et al. "Molecular n-type doping for air-stable electron transport in vacuum-processed n-channel organic transistors." Applied Physics Letters 97, 243305 (Dec. 2010).
P. Wei et al. "Use of a 1*H*-Benzoimidazole Derivative as an *n*-Type Dopant and to Enable Air-Stable Solution-Processed *n*-Channel Organic Thin-Film Transistors." J. Am. Chem. Society 132(26), 8852-8853 (Jun. 2010). Abstract only.
S. Reineke et al. "White organic light-emitting diodes with fluorescent tube efficiency." Nature 459, 234 (May 2009).
J. Liu et al. "Efficient bottom cathodes for organic light-emitting devices." App. Phys. Lett. 85(5), 837 (2004). Abstract only.
S. Tanaka et al. "Doping Effect of Tetrathianaphthacene Molecule in Organic Semiconductors on Their Interfacial Electronic Structures Studied by UV Photoemission Spectroscopy." Jpn. J. Appl. Phys. 44(6a) 3760 (2005).
C. Chan et al. "N-type doping of an electron-transport material by controlled gas-phase incorporation of cobaltocene." Chem. Phys. Lett. 431, 67 (Sep. 2006).
A. Werner et al. "n-Type Doping of Organic Thin Films Using Cationic Dyes." Adv. Funct. Materials 14(3), 255 (Mar. 2004). Abstract only.
F. Li et al. "Leuco Crystal Violet as a Dopant for n-Doping of Organic Thin Films of Fullerene C60." J. Phy. Chem. B 108(44), 17076-17082 (Oct. 2004). Abstract only.
X.Q. Zhu et al. "Hydride, Hydrogen Atom, Proton, and Electron Transfer Driving Forces of Various Five-Membered Heterocyclic Organic Hydrides." J. Am. Chem. Soc. 130(8), 2501-2516 (Feb. 2008). Abstract only.

* cited by examiner

N-TYPE DOPED ORGANIC MATERIALS AND METHODS THEREFOR

RELATED PATENT DOCUMENT

This patent document claims the benefit, under 35 U.S.C. §119(e), of U.S. Provisional Patent Application Ser. No. 61/321,033 filed on Apr. 5, 2010, and entitled "n-Type Doped Organic Materials and Methods Therefor;" this patent document is fully incorporated herein by reference.

FEDERALLY-SPONSORED RESEARCH AND DEVELOPMENT

This invention was made with Government support under contract FA9550-09-1-0256 awarded by the Air Force Office of Scientific Research. The U.S. Government has certain rights in this invention.

FIELD

The present invention relates generally to organic electronic devices, and more specifically, to doped organic electronic devices and related methods.

BACKGROUND

Organic electronic devices, such as organic thin-film transistors (OTFTs) and other organic semiconductors (OSCs) have attracted a great deal of attention because of their potential applications in low-cost, large-area and flexible electronics. Organic semiconductors are commonly referred to as either p-channel (hole-transporting) or n-channel (electron-transporting) depending on which type of charge carrier is dominant for the charge transport.

While p-channel organic semiconductors have been readily implemented for a variety of applications, n-channel organic semiconductors have been challenging to manufacture and implement. Generally, the energetically high-lying lowest unoccupied molecular orbital (LUMO) levels in most organic semiconductors hinder the efficient injection of electrons. In n-channel OTFTs, electrons can be transferred from the high-lying highest occupied molecular orbitals (HOMOs) of dopants to the LUMOs of organic semiconductors by n-type doping. However, such dopants are susceptible to oxidation in air. Electron charge carriers are vulnerable to trapping, either by traps at the interface of dielectric-semiconductor materials, which may involve hydroxyl groups or ambient oxidants, such as $O_2$ and $H_2O$. Such charge-trapping can decrease the density of mobile electron charge carriers, degrade the mobility, and increase the threshold voltage for n-channel OTFTs.

While various n-type dopants have been used to dope organic semiconductors, they have been challenging to implement. For example, alkali metals are prone to diffuse through organic layers due to their relatively small atomic radii, leading to device instability. In addition, alkali metals are difficult to process. Other dopants having both extremely high-lying HOMO levels and exhibiting air stability do not provide donors that are strong enough to obtain sufficient n-channel conductivity. Cationic dyes have been used as stable precursors for strong molecular donors, but have been relatively limited due to the lack of available compounds having a strong n-type doping effect.

These and other issues remain as a challenge to a variety of methods, devices and systems that use or benefit from organic semiconductors, such as organic thin-film transistors, organic light-emitting diodes (OLEDs), and organic photovoltaics (OPVs).

SUMMARY

Various aspects of the present disclosure are directed to devices, methods and systems involving doped materials used in semiconductors, which address challenges including those discussed above.

According to an example embodiment, an organic electronic device includes an organic material and an n-type dopant material. The n-type dopant material is a portion of the organic material, and includes an imidazole-based material including a hydrogen-based material bonded between nitrogen atoms.

In another embodiment, the dopant material includes an imidazole-based material that has a hydrogen-based material bonded between nitrogen atoms, and where the imidazole-based material is configured to n-dope organic semiconductor materials.

In another embodiment, a method for manufacturing an organic-material device includes introducing an n-type dopant material to an organic material, and using the n-type dopant material to dope the organic material. The n-type dopant, in such an embodiment, includes an imidazole-based material having a hydrogen-based material bonded between nitrogen atoms.

Another example embodiment is directed to an organic semiconductor device. The device includes a substrate, a gate electrode, a gate oxide on the gate electrode, and an organic semiconductor material over the gate oxide. A passivation layer including BCB (divinyltetramethyldisiloxane bis(benzocyclobutene)) is located on the gate oxide and between the gate oxide and the organic semiconductor material. This passivation layer is configured to mitigate oxidation at an interface region between the gate oxide and the organic semiconductor material. The device further includes source and drain electrodes and, in a portion of the organic material, a channel being configured to electrically couple the source and drain electrodes. The channel region has a surface region having impurities that trap electron charge carriers and mitigate charge transport between the source and drain electrodes, and an n-type dopant material. The n-type dopant material includes an imidazole-based material with a hydrogen-based material bonded between nitrogen atoms, and is configured to increase the mobility of the organic material to compensate for decreased mobility due to the trapped electron charge carriers.

In accordance with other example embodiments, an organic electronic device is manufactured as follows. An n-type dopant material, which includes an imidazole-based material having a hydrogen-based material bonded between nitrogen atoms, is introduced to an organic material. The n-type dopant material is then used to dope the organic material.

Another example embodiment is directed to a dopant material comprising an imidazole-based material including a hydrogen-based material bonded between nitrogen atoms, in which the imidazole-based material is configured to n-dope organic semiconductor materials.

Another example embodiment is directed to an organic thin-film device at an intermediate stage of manufacture. The device includes a substrate and, on the substrate, a solution including an n-type dopant having an imidazole-based material therein mixed with an organic matrix material. The imidazole-based material includes a hydrogen-based material bonded between nitrogen atoms, and the solution configured to form an organic channel layer doped with a dopant from the imidazole-based material. Depending on the application, more specific embodiments can be implemented with the dopant being either blended with the matrix material or in contact with the matrix material.

According to another example embodiment, an organic electronic device includes an organic material and a p-type dopant material. The p-type dopant material is a portion of the organic material, and includes an imidazole-based material including a material bonded between atoms therein as characterized by what is referred to herein as Formula B.

The above summary is not intended to describe each embodiment or every implementation of the present disclosure. The figures and detailed description that follow more particularly exemplify various embodiments.

BRIEF DESCRIPTION OF THE DRAWINGS

Aspects of the invention may be more completely understood in consideration of the following detailed description of various embodiments of the invention in connection with the accompanying drawings, in which.

FIG. 1 (including FIGS. 1A-1H) shows organic semiconductor devices and various materials used therein, according to an example embodiment of the present invention;

While aspects of the invention are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

The present invention relates to organic semiconductors and methods for making organically-based materials useful with semiconductors and semiconductor devices, as described herein. Certain aspects of the present disclosure have been found to be particularly beneficial and useful in connection with doped organic semiconductors. The disclosure is not, however, so limited. For example, aspects of the present disclosure have also been found to be particularly beneficial and useful with organic memory (as in organic electric devices) and with carbon-related devices such as carbon nanotubes and graphene-based devices. While the present invention is not necessarily limited in these contexts, various aspects of the invention may be appreciated through a discussion of examples using these and other contexts.

According to an example embodiment of the present invention, an organic device includes an imidazole-based dopant material that is configured to n-type dope a material such as an organic material. The n-type doped organic material has an increased mobility, relative to undoped portions of the organic material. This increased mobility can be used to offset decreases in mobility of the organic material due to charge trapping, such as may be effected by impurities, oxidation or other conditions relating to the exposure of the organic device to an ambient atmosphere.

In connection with other example embodiments, an organic device is manufactured using an imidazole-based dopant material. The imidazole-based dopant material is used to dope an organic material in the organic device. In some implementations, the dopant material is used as a precursor to generate radicals with high-lying energy levels, which are used to dope the organic material. For general information regarding radical generation, and for specific information regarding radical generation as may be implemented in connection with one or more example embodiments, reference may be made to Chan, C. K., Kim, E. G., Bredas, J. L. & Kahn, A., "Molecular n-type Doping of 1,4,5,8-naphthalene tetracarboxylic dianhydride by Pyronin B Studied Using Direct and Inverse Photoelectron Spectroscopies," *Adv. Funct. Mater.* 16, 831-837 (2006), which is fully incorporated herein by reference.

In some embodiments, imidazole-based dopants are introduced to an organic semiconductor material to increase the charge carrier density and reduce ohmic losses in organic devices in which the organic semiconductor material is employed, facilitating desirable film mobility and charge carrier mobility therein. The dopants can be vacuum deposited and/or solution processed to dope and set electric characteristics of the organic semiconductor (or conductor) matrix materials. The dopants are used to effect an n-type molecular doping, under relatively low-temperature conditions, and are relatively stable in air (e.g., resistant to oxidation). Electrons are transferred from the high-lying highest occupied molecular orbitals (HOMOs) of dopants to the lowest unoccupied molecular orbitals (LUMOs) of organic semiconductors via n-type doping. The density of mobile electron charge carriers in the organic semiconductor is increased to compensate for the trapped electrons by ambient oxidants, resulting in the decrease of the threshold voltages and improvement of the air stability for devices. For general information regarding organic devices, and for specific information regarding doping organic devices to increase charge carriers, reference may be made to Walzer, K., Maennig, B., Pfeiffer, M. & Leo, K., "Highly efficient organic devices based on electrically doped transport layers," *Chem. Rev.* 107, 1233-1271 (2007), cited below and fully incorporated herein by reference.

The doping effect (and strength) can be controlled using different substitution approaches to suit particular designs employing the doped organic substrates. For example, electron-donor and/or electron-acceptor group-based substitution can be carried out to suit the needs of particular applications. These approaches can be used with a variety of organic electronic devices such as organic light-emitting diodes (OLEDs), organic thin-film transistors (OTFTs), solar cells, photovoltaic devices and other organic semiconductors (OSCs).

In some implementations, one or more 1,3-dimethyl-2-phenyl-2,3-dihydro-1H-benzoimidazole (DMBI) derivatives are respectively implemented to dope organic semiconductors via different types of substitution. In connection with these embodiments, it has been discovered that these DMBI derivatives exhibit a relatively strong doping effect, and can result in a significant increase in the conductivity of the organic semiconductors (e.g., increases of 3 or more orders of magnitude). For general information regarding dopant materials, and specific information regarding DMBI derivative materials and/or their application as may be implemented in connection with one or example embodiments, reference may be made to Tanner, D. D. & Chen, J. J., "On the Mechanism of the Reduction of Alpha-halo Ketones By 1,3-dimethyl-2-phenylbenzimidazoline-reduction by a Set-hydrogen Atom Abstraction Chain Mechanism," *J. Org. Chem.* 54, 3842-3846 (1989), cited below and fully incorporated herein.

In a more particular implementation, DMBI derivatives are used to dope n-channel OTFTs, and are used to compensate for the trapped electron charge carriers. Such OTFTs may include, for example, those with a solution-processable n-channel organic semiconductor, [6,6]-phenyl C61-butyric acid methyl ester (PCBM). Threshold voltages of n-channel OTFTs decrease and air stability increases, upon doping.

In connection with various example embodiments, an organic device is manufactured under conditions that involve the exposure of an organic material therein to air. The organic material exhibits a decrease in charge carriers in response to the exposure (e.g., in an undoped state). An n-dopant is used to dope the organic material to compensate for the decreased mobility of the organic material, such as to render the mobility of the doped organic material similar to the mobility of the doped material as manufactured under inert conditions. In some implementations, the manufacturing approach involves not manufacturing the organic device in an inert environment, thus avoiding expense and other undesirable characteristics of the manufacture of such devices.

Turning now to the figures, FIG. 1 shows an organic semiconductor device and various materials used therein, in accordance with one or more example embodiments of the present invention. FIG. 1A shows exemplary imidazole derivatives that are used as n-type dopants, including the specific chemical structures of 1,2,3-trimethyl-2-phenyl-2,3-dihydro-1H-benzoimidazole (TMBI, as reference), and four DMBI derivatives having different substitutions including electron acceptor and donor moieties. The DMBI derivatives include DMBI, dichlorophenyl)-1,3-dimethyl-2,3-dihydro-1H-benzoimidazole (Cl-DMBI); (4-(1,3-dimethyl-2,3-dihydro-1H-benzoimidazole-2-yl)-phenyl)-dimethyl-amine (N-DMBI); and 2-(1,3-dimethyl-2,3-dihydro-1H-benzoimidazol-2-yl)-phenol (OH-DMBI).

Figure 1A:
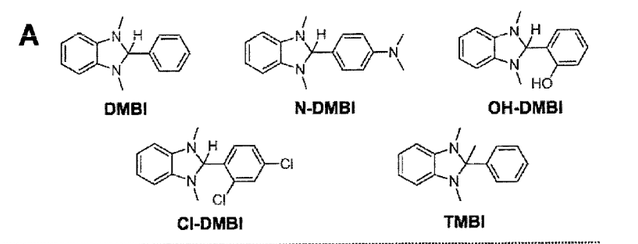
Figure 1B:
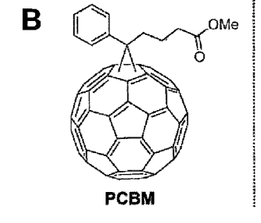
Figure 1C:
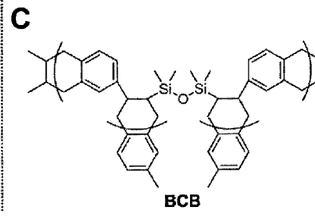

FIG. 1B shows the chemical structure of solution processable n-channel organic semiconductor PCBM, and FIG. 1C shows the chemical structure of thermally crosslinked hydroxyl-free BCB (divinyltetramethyldisiloxane bis(benzocyclobutene)) used as a dielectric for the organic semiconductor. The PCBM shown in FIG. 1C exemplifies one of a multitude of different types of organic semiconductors to which various embodiments are amenable for implementation with.

Figure 1D:
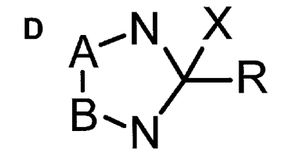

FIG. 1D shows a chemical structure for an imidazole-based material, used as an n-type dopant material for doping of organic materials, in connection with one or more embodiments. The imidazole-based material includes one or more $sp^3$- or $sp^2$-hybridized carbon atoms as A and B. The symbol R represents an H atom or alkyl, aryl groups. The symbol X may be implemented using an H atom. In various embodiments consistent with the present disclosure, for all such R groups (R1, R2 and R3), thiophenes and other aromatic rings are considered within the aryl groups, such as shown FIG. 1G and with the alkyl group for the structures shown in FIG. 1H.

Figure 1E:
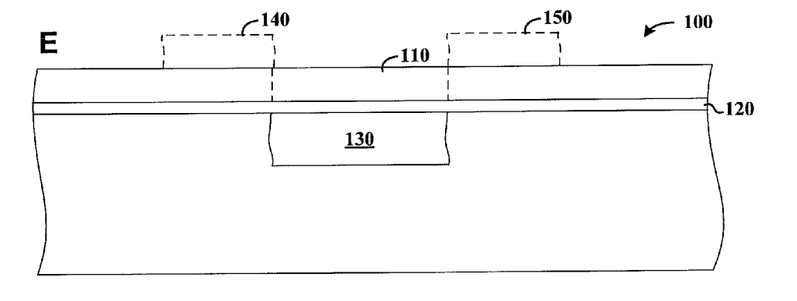

FIG. 1E shows an organic semiconductor device 100, having a PCBM-based organic semiconductor channel 110 doped using one or more of the imidazole derivatives shown in FIG. 1A, and having a dielectric layer 120 including a thermally crosslinked hydroxyl-free BCB type of material (e.g., on an oxide such as $SiO_2$), in accordance with one or more example embodiments. An electrode 130 is configured for applying a bias to the channel 110, via the dielectric material 120, which respectively can be used in a variety of semiconductor applications. For example, the device 100 may include source/drain regions 140/150 for implementation as an OTFT. In addition, while the device 100 is shown in a back-gate type of arrangement, the materials shown therein as well as in FIGS. 1A-1C may be implemented in a front-gated configuration as well, with the electrode 130 arranged over a dielectric and underlying channel region, the channel region being formed in or on an underlying substrate (e.g., the respective components inverted).

Figure 1F:
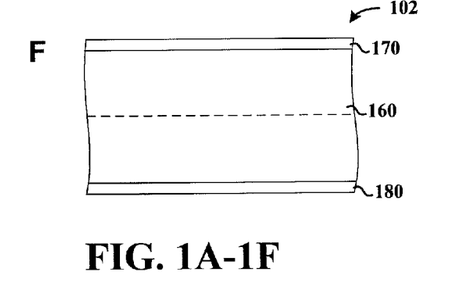
Figure 1G:
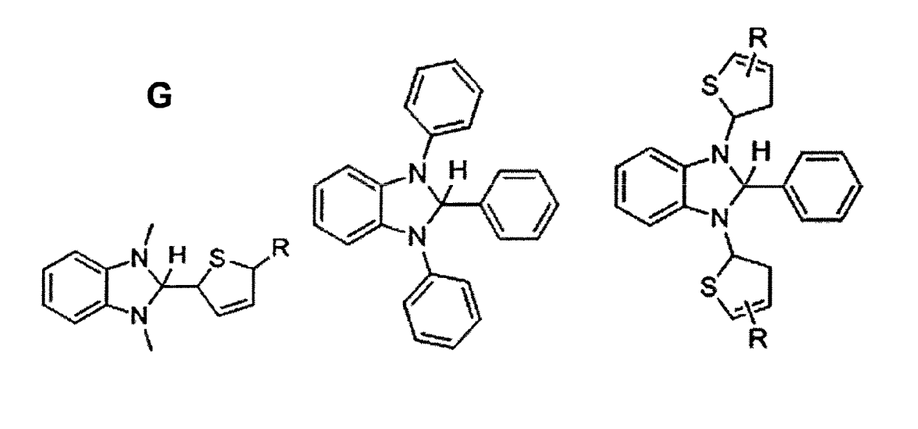
Figure 1H:
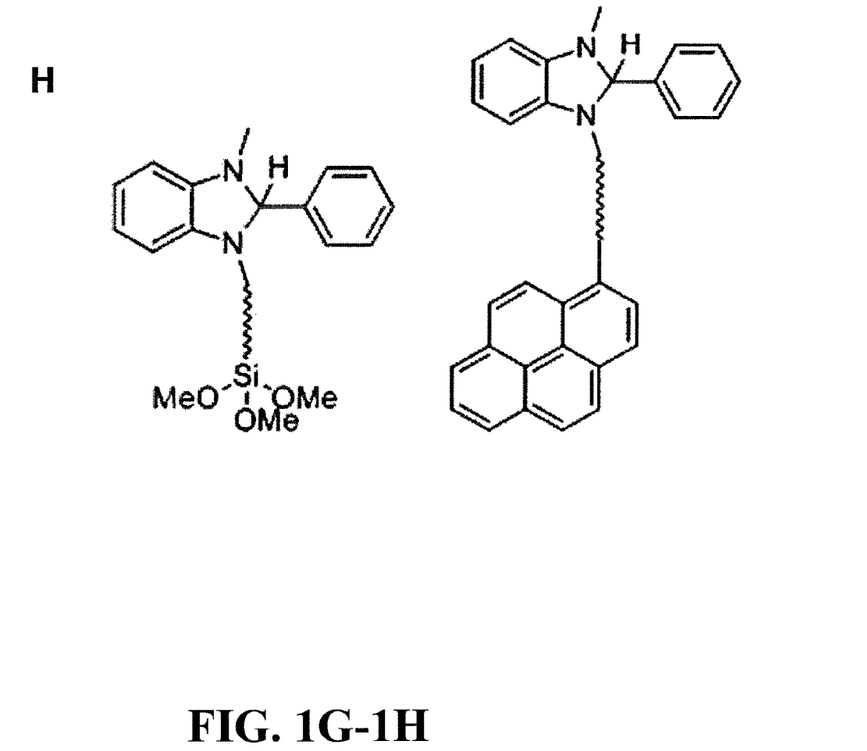

FIG. 1F shows an organic optical device 102, in accordance with another example embodiment. The device 102 may, for example, be implemented as an organic light-emitting diode (OLED) device, as an organic photovoltaic device, or as layers of one or more other optical devices. The device 102 includes an organic semiconductor layer 160 that is n-doped as discussed above, and electrodes 170 and 180. In some applications, the organic semiconductor layer 160 includes two layers of material separated as shown by a dashed line, with the layers respectively acting as emissive and conductive layers (or donor/acceptor layers), and selectively including additional and/or other materials. Other embodiments involve the mixing of layers and/or introduction of other layers, as appropriate for particular organic semiconductor applications.

Figure 2:
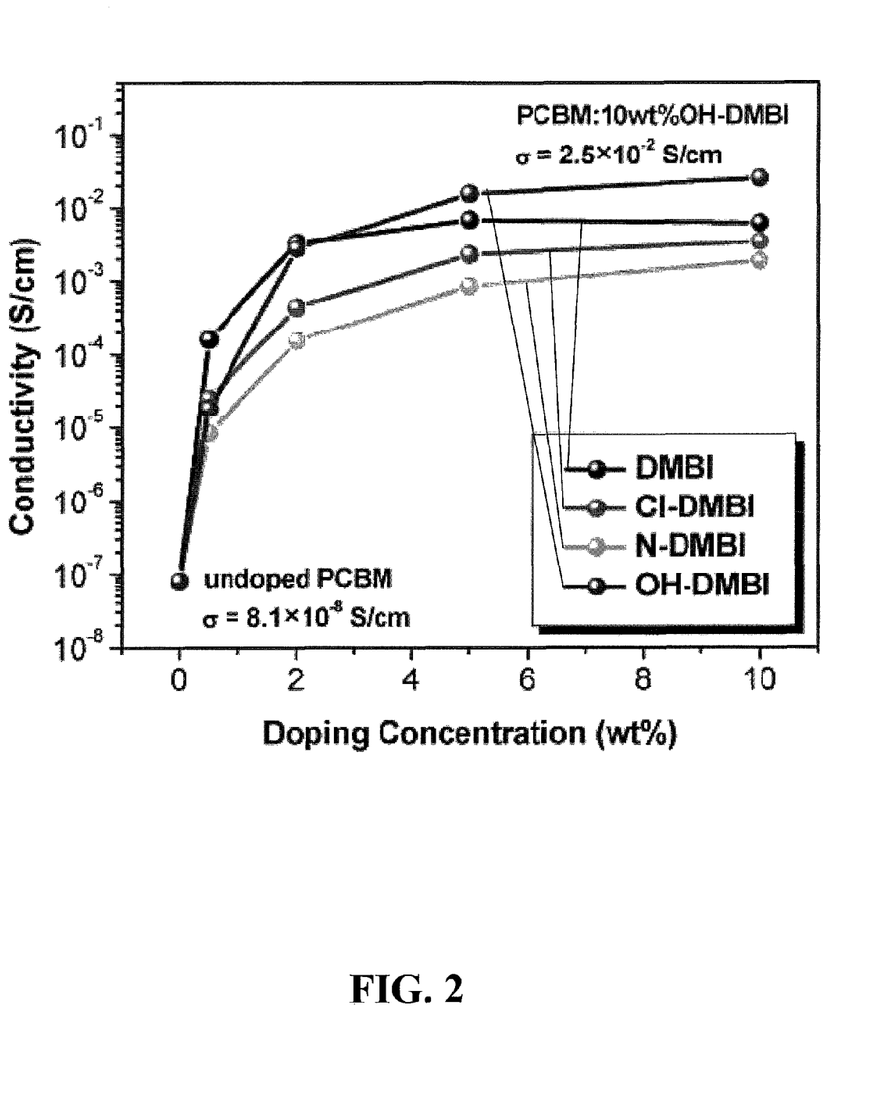
FIG. 2 shows plots of n-type doping effects of DMBI derivatives shown in FIG. 1, in accordance with other example embodiments.

FIG. 2 shows plots of n-type doping effects of the four DMBI derivatives shown in FIG. 1, in connection with one or more example embodiments. The dopants are used to increase the respective conductivities of doped films significantly (by at least two orders of magnitude), which can be effected at a low doping concentration of about 0.5 wt % for these four DMBI derivatives. A semiconductor conductivity of about $2.5 \times 10^{-2}$ S/cm can be achieved at about 10 wt % doping of OH-DMBI on PCBM (almost six orders of magnitude higher than the undoped PCBM film). In connection with these embodiments and as exemplified in FIG. 2, it has also been discovered that the dependence of the conductivities of the resulting films upon doping concentrations is not linear. For example, at high doping concentrations (5 wt % and 10 wt % doping), the conductivities do not increase as much as the respective conductivities at lower doping concentrations (0.5 wt % and 2 wt %), and may exhibit a decrease in conductivity at certain concentrations (e.g., for 10 wt % DMBI doped PCBM film, the dopant may disturb the matrix lattice, or donated electrons may be localized (as relative to carrier transport in organic versus inorganic materials by hopping mode), resulting in decreased conductivity). As consistent with the morphology of the doping films, these DMBI dopants tend to aggregate in the films, particularly at relatively high doping concentrations, so that this strong n-type doping effect cannot extend and then delocalize to the whole doped films.

Figure 3:
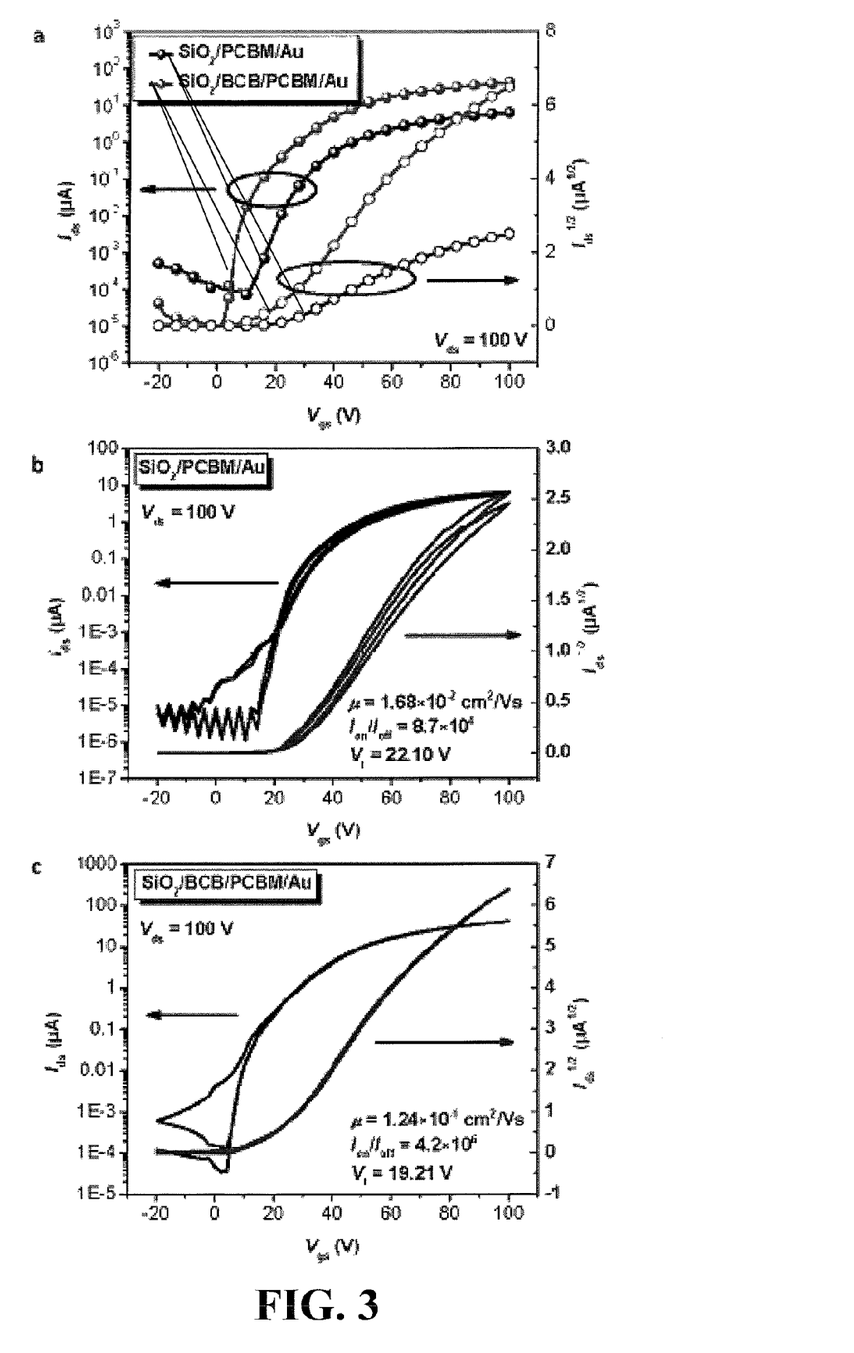
FIG. 3 shows plots of transfer and hysteresis characteristics of transistors, in accordance with other example embodiments.

FIG. 3 shows plots of transfer and hysteresis characteristics of PCBM OTFTs with/without a BCB interlayer (Vds=100 V), measured in an $N_2$ environment ($O_2$, $H_2O<0.1$ ppm), for organic devices in accordance with other example embodiments. The plots are shown for PCBM transistors having a bottom-gate, top-contact configuration, similar to the OTFT transistor shown in FIG. 1E. To facilitate discussion of these embodiments, the following discussion refers back to FIG. 1E.

Gold (Au) is used as source and drain electrodes 140/150 with the dielectric layer 120 including a thin (20 nm) thermal crosslinked BCB layer covered on the surface of a 300 nm thick $SiO_2$ dielectric to passivate the dielectric/semiconductor interface and reduce/eliminate electron charge carrier traps, such as those involving hydroxyl groups. An order of magnitude increase in electron mobility ($\mu=1.24\times10^{-1}$ cm$^2$/Vs) can be obtained using the PCBM with the BCB interlayer (e.g., in $N_2$) as shown in FIG. 3A, as compared with a pristine (e.g., undoped) PCBM device ($\mu=1.68\times10^{-2}$ cm$^2$/Vs). The transistor with BCB also exhibits a threshold voltage Vt of 19.21 V, which is lower than that of a pristine PCBM device (Vt=22.10 V).

FIGS. 3B and 3C respectively show hysteresis characteristics of devices without and with a BCB interlayer, with electron traps at the dielectric/semiconductor interface mitigated via passivation of the hydroxyl-free BCB interlayer. These interlayers can be n-type doped with to obtain solution processable n-channel transistors with high performance and good air stability.

Figure 4:
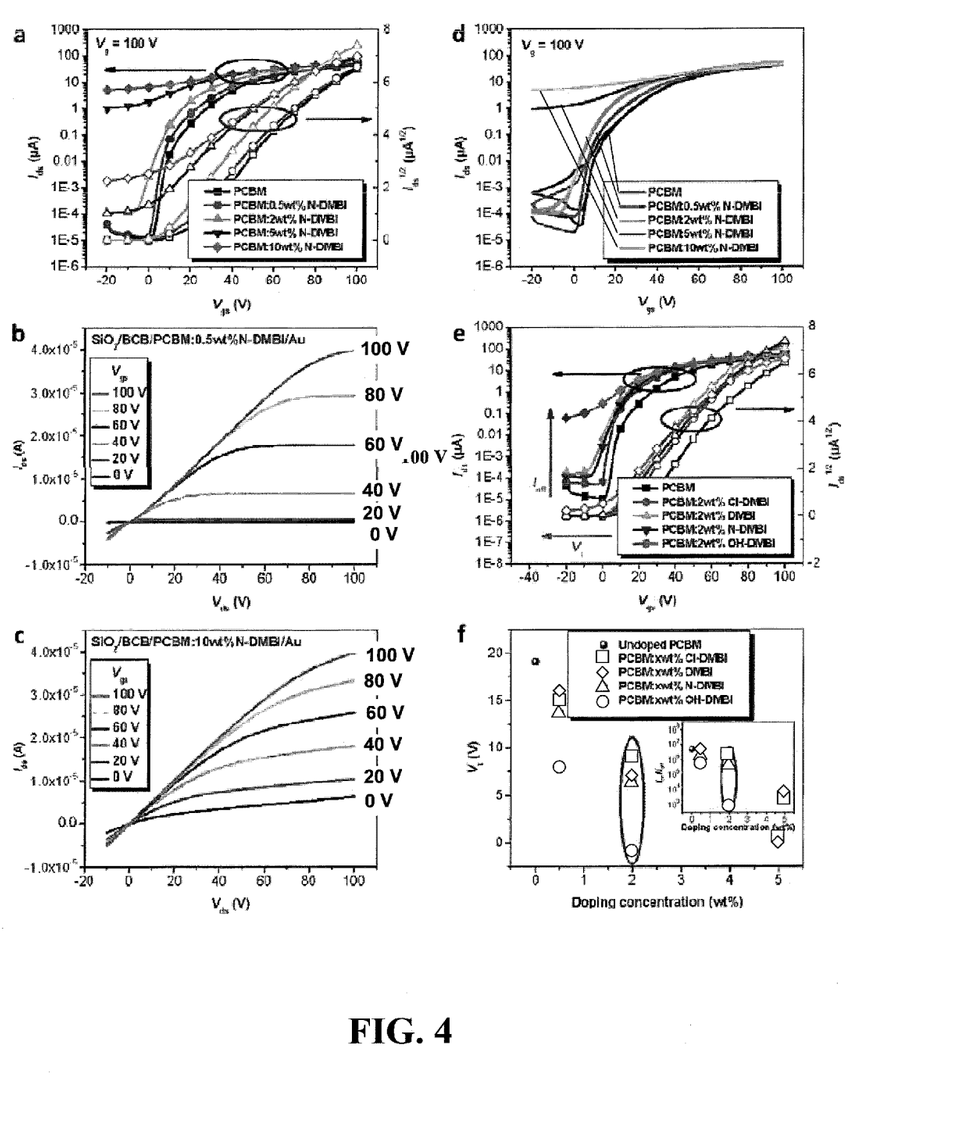
FIG. 4 shows plots of representative transfer, output, hysteresis and doping effect for organic semiconductor devices, in connection with various example embodiments.

FIG. 4 shows plots of representative OTFT transfer, output and hysteresis characteristics of N-DMBI doped PCBM devices, and the n-type doping effect on PCBM transistors with different dopants and at different doping concentrations (as obtained in an $N_2$ environment), in connection with various example embodiments. The plotted characteristics may, for example, be commensurate with the transistors represented in Table 1 below. FIG. 4A shows transfer (Vds=100 V) characteristics of N-DMBI doped PCBM transistors at different doping concentrations. FIG. 4B shows output characteristics of 0.5 wt % N-DMBI-doped PCBM transistors. FIG. 4C shows output characteristics of 10 wt % N-DMBI doped PCBM transistors. FIG. 4D shows hysteresis characteristics of N-DMBI doped PCBM transistors at different doping concentrations. FIG. 4E shows transfer (Vds=100 V) characteristics of doped PCBM transistors with four DMBI derivatives at the doping concentration of 2 wt %. FIG. 4F shows threshold voltages of doped PCBM transistors with four DMBI derivatives at different doping concentrations, with the inset showing on-off ratios of the doped PCBM transistors with four DMBI derivatives at different doping concentrations.

The threshold voltage Vt of transistors can be used to evaluate the gate bias (Vgs) at which electron trap states have been filled and the carriers become mobile. From the transfer characteristics of the doped PCBM transistors, Vt is systematically shifted in negative direction with the increase of the doping concentration for each DMBI dopant, which may be due to the availability of additional mobile electrons obtained after n-type doping. For four DMBI derivatives, the order of the negative shift and the decrease of the on-off ratio is Cl-DMBI<DMBI<N-DMBI<OH-DMBI, which is the same as the trend of HOMO energy levels except OH-DMBI (CL-DMBI: −4.76 eV, DMBI: −4.73 eV, N-DMBI: −4.67 eV, OH-DMBI: −4.74 eV).

In connection with these embodiments, it has been discovered that the n-type doping strength can be effectively tuned by substituting DMBI derivatives with electron acceptor and donor moieties. At a low doping concentration, the mobilities of doping devices are kept at about 0.1 cm$^2$/Vs, and on-off ratios and Vt decrease relative to undoped devices. At a higher doping concentration of 10 wt %, the doped PCBM devices are nearly conductive such that off currents are higher than about 0.5 µA and on-off ratios are lower than 1000. The 10 wt % OH-DMBI doping transistor exhibits a high off current of about 1.4 µA and a low on-off ratio of about 20. Substantially no hysteresis is exhibited by the doped transistors, even at a high doping concentration.

In an experimental-type embodiment, the doping effect is compared with reported n-type dopants, by fabricating doped PCBM transistors with leucocrystal violet (LCV). Doping effects, such as the negative shift of threshold voltage and the decrease of on-off ratio, are mitigated. The n-type doping effect of OH-DMBI on PCBM transistors may exclude or mitigate contributions to the doping effect via charge carrier injection from contacts on negative shifts, and the decrease of the on-off ratio, (e.g., HOMO levels of OH-DMBI are observed as insignificantly different from that of the other three DMBI derivatives).

Table 1 shows performance characteristics of PCBM transistors fabricated at different doping concentrations using four dopants including different DMBI derivatives and TMBI, as measured in an $N_2$ environment, in connection with various example embodiments. The mobilities at high doping concentrations are not shown (the devices are almost conductive and the on-off ratios are lower than 1000). The data shown represent averages obtained from three or more devices.

TABLE 1

| | Glovebox | | |
|---|---|---|---|
| | $\mu^a$ (cm$^2$/Vs) | $I_{on}/I_{off}$ | $V_t$ (V) |
| PCBM | $1.25 \times 10^{-1}$ | $4.67 \times 10^6$ | 19.10 |
| PCBM: 0.5 wt % Cl-DMBI | $1.27 \times 10^{-1}$ | $3.87 \times 10^6$ | 15.28 |
| PCBM: 2 wt % Cl-DMBI | $1.27 \times 10^{-1}$ | $1.73 \times 10^6$ | 8.95 |
| PCBM: 5 wt % Cl-DMBI | $0.94 \times 10^{-1}$ | $4.00 \times 10^3$ | 0.70 |
| PCBM: 10 wt % Cl-DMBI | / | / | / |
| PCBM: 0.5 wt % DMBI | $1.55 \times 10^{-1}$ | $3.77 \times 10^6$ | 15.82 |
| PCBM: 2 wt % DMBI | $1.57 \times 10^{-1}$ | $5.40 \times 10^5$ | 6.99 |
| PCBM: 5 wt % DMBI | $1.02 \times 10^{-1}$ | $7.20 \times 10^3$ | 0.53 |
| PCBM: 10 wt % DMBI | / | / | / |
| PCBM: 0.5 wt % N-DMBI | $1.18 \times 10^{-1}$ | $2.73 \times 10^6$ | 13.73 |
| PCBM: 2 wt % N-DMBI | $1.02 \times 10^{-1}$ | $4.77 \times 10^5$ | 6.43 |
| PCBM: 5 wt % N-DMBI | / | / | / |
| PCBM: 10 wt % N-DMBI | / | / | / |
| PCBM: 0.5 wt % OH-DMBI | $1.86 \times 10^{-1}$ | $9.73 \times 10^6$ | 7.90 |
| PCBM: 2 wt % OH-DMBI | $1.00 \times 10^{-1}$ | $6.70 \times 10^2$ | −1.03 |
| PCBM: 5 wt % OH-DMBI | / | / | / |
| PCBM: 10 wt % OH-DMBI | / | / | / |
| PCBM: 0.5 wt % TMBI | $1.07 \times 10^{-1}$ | $3.30 \times 10^6$ | 18.31 |
| PCBM: 2 wt % TMBI | $1.22 \times 10^{-1}$ | $5.27 \times 10^6$ | 26.76 |

Doping as discussed herein is carried out using a variety of approaches and mechanisms. In some implementations, the DMBI derivatives are used as precursors for doping, and act as hydrogen transfer reagents to donate hydrogen or hydride with the existence of a reductant, and form radicals with high-lying HOMOs of the dopant material. In connection with these embodiments, it has been discovered that this hydrogen transfer and high energetic radicals can be used to effect strong n-type doping effect of DMBI derivatives.

Other experimental-type embodiments are directed to detecting the doping of organic semiconductor materials as discussed above. By theoretical calculations (Gaussian 03', B3LYP/6-31G*), the HOMO levels of four DMBI radicals are obtained as −3.05 eV of CL-DMBI, −2.73 eV of DMBI, −2.36 eV of N-DMBI and −2.55 eV of OH-DMBI, which are all high and used to make the electron transfer much easier from the HOMOs of DMBI radicals to the LUMO of PCBM. The order of the HOMO levels is also the same as that of the doping effect on PCBM transistors, except for OH-DMBI. The DMBI cation shows a generally planar configuration (relative to DMBI) after hydrogen transfer and electron transfer, which is used to obtain a stable n-type doping effect.

The doping effect is compared by replacing a 2-position hydrogen at the imidazole core with a methyl group, which is not as easy to be removed as the hydrogen atom. In this context, 1,2,3-trimethyl-2-phenyl-2,3-dihydro-1H-benzoimidazole (TMBI) doped PCBM transistors are fabricated with different doping concentrations, as represented in Table 1. Negative Vt shift and the decreasing on-off ratio n-type doping effects in devices are not observed.

In connection with these experimental embodiments, it has also been discovered that, among the four DMBI dopants, OH-DMBI exhibits a strongest n-type doping effect, although the HOMO levels of molecule and radical are not the highest. Measuring the capacitance-voltage characteristics of $Si/SiO_2$/undoped and doped PCBM/Au metal-insulator-semiconductor (MIS) diodes with DMBI and OH-DMBI, electron densities can be extracted according to the standard Schottky-Mott analysis (see, e.g., references 32-34 below). For undoped PCBM diodes, the electron density is about $3.42 \times 10^{17}/cm^3$. With 10 wt % DMBI doping, the electron density increases about 5 times to $1.43 \times 10^{18}/cm^3$, and with 10 wt % OH-DMBI doping, the electron density increases to $9.02 \times 10^{18}/cm^3$, which is higher than undoped and DMBI-doped PCBM diodes, indicating OH-DMBI can donate more electrons than DMBI even with similar HOMO levels for both neutral molecules and radicals. This doping can be carried out using OH-DMBI as a two-electron-donor in which the hydroxyl group serves as a second hydrogen abstraction source.

Figure 5:
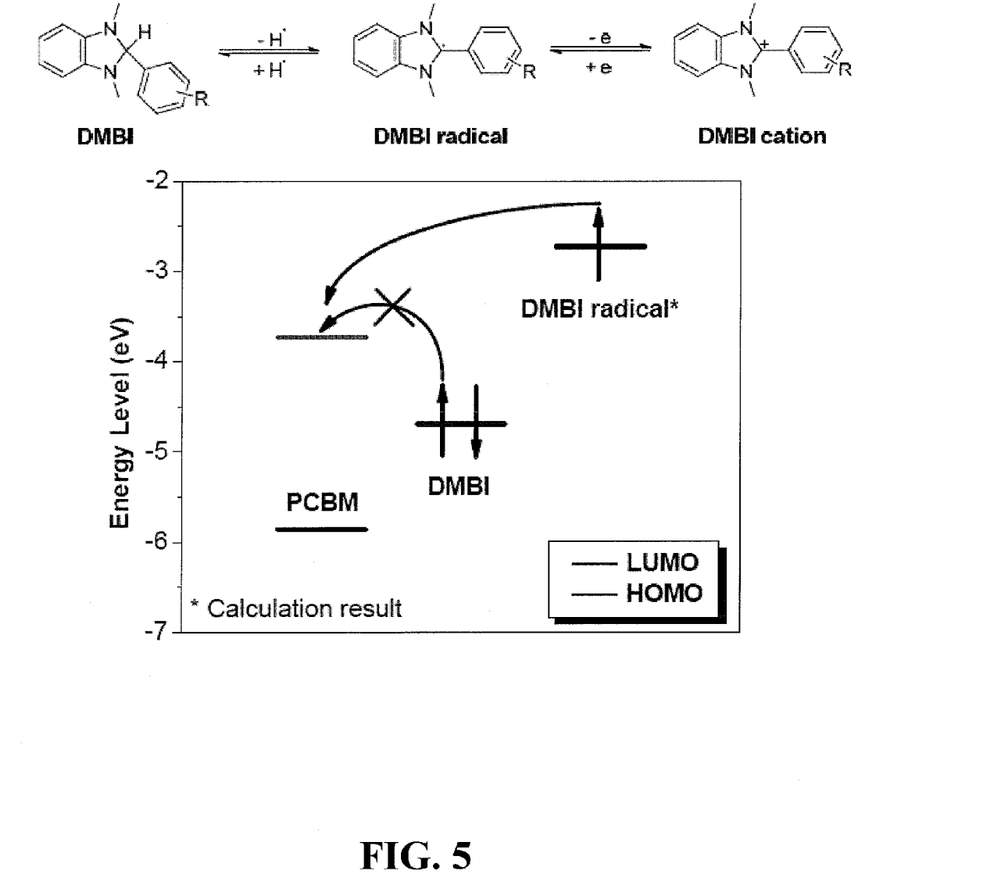
FIG. 5 shows DMBI-based molecules and an energy diagram-plot showing hydrogen transfer and electron transfer for n-type doping with PCBM, DMBI and DMBI radicals, in accordance with other example embodiments.

FIG. 5 shows DMBI-based molecules and an energy diagram-plot showing hydrogen transfer and electron transfer for n-type doping with PCBM, DMBI and DMBI radicals, in accordance with other example embodiments. For a neutral DMBI molecule, the HOMO level is lower than the LUMO of PCBM, so that the electron transfer from DMBI to PCBM is not easy to process. However, after the abstraction of a hydrogen atom, the DMBI radical has a high-lying HOMO level, which is used to facilitate electron transfer. In some embodiments, n-type doping as represented in FIG. 5 and/or otherwise described herein can be used to compensate for electrons trapped by ambient oxidants, leading to an improvement in the air stability of n-channel OTFTs employing such doping/dopants.

Figure 6:
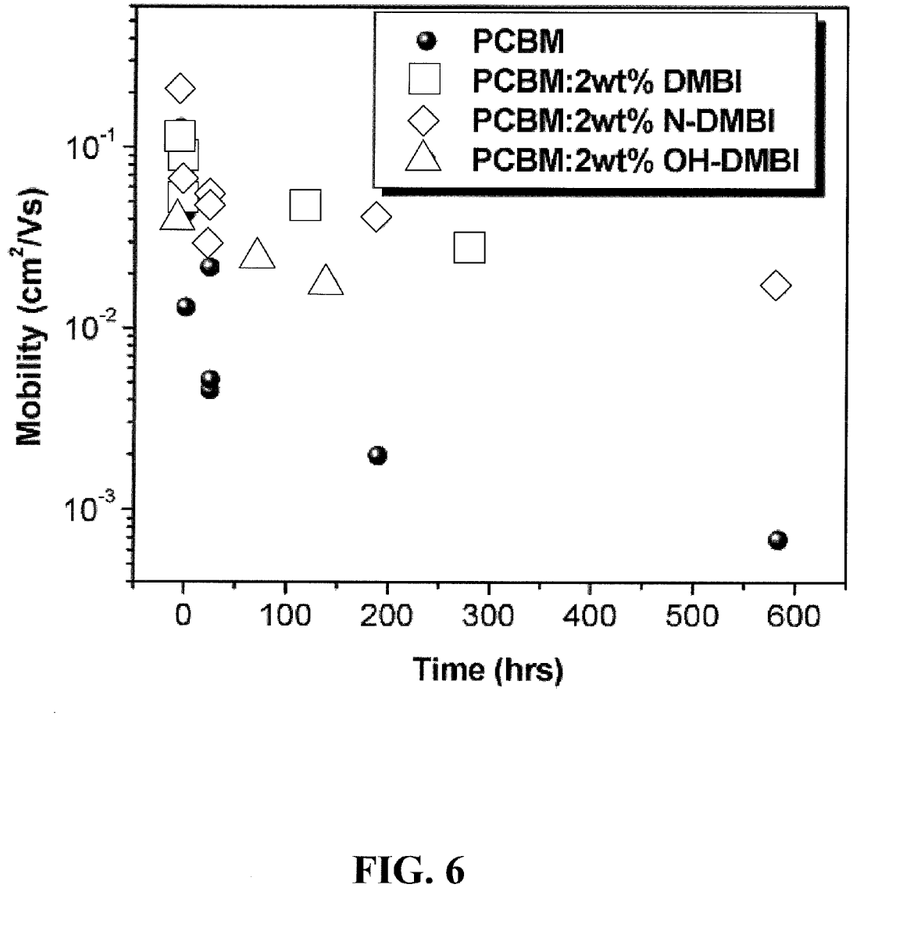
FIG. 6 shows long-term air stabilities of undoped PCBM and DMBI derivative-doped transistors, in accordance with other example embodiments.

FIG. 6 shows long-term air stabilities of undoped PCBM and DMBI derivative-doped transistors, in accordance with other example embodiments. The performance is plotted as a function of time for transistors respectively employing DMBI, N-DMBI and OH-DMBI dopants at 2 wt %, as well as undoped PCBM. For the undoped PCBM, the performance degrades quickly, though the interface of dielectric/semiconductor may already be passivated by a thin hydroxyl-free BCB layer. Operation of the PCBM transistor without BCB passivation can result in termination of device functionality in about 5 minutes after exposure to air, which may be due to rapid electron charge trapping by ambient oxidants (e.g., due to the high-lying LUMO level of PCBM). Doping with n-type DMBI derivatives improves the air stability and maintains the mobility (e.g., higher than $10^{-2}$ $cm^2$/Vs), which renders the doping approach amenable for use with air sensitive n-channel semiconductors.

According to another aspect of the present disclosure, such n-type doping is used to effect carbon-related devices such as carbon nanotubes and graphene-based devices. For carbon nanotubes and graphene structures, for example, the Fermi level therefor should be below −2.5 eV to effect such n-type doping. According to a more specific aspect with an imidazole-based material (as illustrated and described herein), R1 includes at least one of an H atom, an alkyl group, an aralkyl group, an sp2-hybridized carbon atom bonded group and borane, R2 and R3 include at least one of and H atom and at least one sp3- or sp2-hybridized carbon atom bonded group and X includes an H atom. An sp2-hybridized carbon atom bonded group is useful in connection with consideration of a heterocyclic group such as thiophenes, pyridine, and some 5- or 6-member rings which are not aromatic such as . An sp3-hybridized carbon atom bonded group is useful in connection with consideration of a halogenated alkyl group, thiol group, or the like.

Consistent herewith, another aspect of this disclosure is directed to a device that includes an organic material which has, in a portion thereof, an n-type dopant material including an imidazole-based material with a hydrogen-based material bonded between nitrogen atoms. The n-type dopant material includes an imidazole-based material that has the formula:

(Formula A)

in which A and B include at least one of $sp^3$- and $sp^2$-hybridized carbon atoms, R1 includes at least one of an H atom, an alkyl group, an aryl alkyl group, an sp2-hybridized carbon atom bonded group and borane, R2 and R3 include at least one of an H atom and at least one sp3- or sp2-hybridized carbon atom bonded group and X includes an H atom. Such an organic-material device can be an electronic or other device, including but not limited to a carbon nanotube-based structure and a graphene structure.

Another aspect of the present disclosure is directed to an alternative structure which relates to the above structure of Formula A. In this alternative structure, the Ns in the above structure of Formula A can be replaced by O and S atoms for n-type dopants, such as as alternatives such that the new embodiments are represented with these replacements as new embodiments Surprisingly, the n-type doping effect of the imidazole derivatives can be effectively tuned by electron donating/withdrawing substituents. By Gaussian 03' calculation, the singly occupied molecular orbitals (SOMO) of the 1,3-dimethyl-2-phenyl-2,3-dihydro-1H-benzoimidazoles' (DMBI)

radicals change with the property of the substitution on the 2-phenyl group in DMBI derivatives. With stronger electron-donating substitutions such as —OH or —NMe2 group, the SOMO level manifests an increase from −2.73 eV to −2.55 eV or −2.36 eV, respectively. On the contrary, with electron-withdrawing substitutions such as —Cl or —F atom, the SOMO level of DMBIs can decrease to −3.05 eV or −3.17 eV, respectively. Because the electron donating process is performed from the SOMO of DMBI radicals to the lowest unoccupied molecular orbital (LUMO) of organic semiconductor, the DMBI derivatives with electron donating substituents show stronger n-type doping effect.

For DMBI derivatives, it has been discovered that when they are doped to the p-channel organic semiconductors, carbon nanotube or graphene, their devices were found to show re-channel performance, but their p-channel performance was quenched due to the strong n-type doping ability of DMBI derivatives. In this regard, the ambipolar transporting ability is not readily achieved by the doping method and, thus there can be significant benefit in developing n-type dopants with lower n-type doping ability based on the backbone of DMBI derivatives to achieve ambipolar transporting ability; this can be important for the development of complex digital circuits, enabling the fabrication of electronic circuits such as complementary inverters without relying on advanced patterning techniques. There is, therefore, an appreciation of having related embodiments with electron-withdrawing or low electron-donating groups/atoms so that the doping ability of the compounds can be effectively tuned.

There are reports on the study of the enthalpy changes of five-member heterocyclic compounds including DMBIs and their derivatives with the replacement of one N atom by S and O atoms (FIG. 1) as one-electron reducing agents in organic redox reactions (Zhu X. Q., et al., *J. Am. Chem. Soc.* 2008, 130, 2501). The molecular structures of the five-member heterocyclic compounds are:

It was found that DMBI derivatives were strong one-electron reducing agents. On the contrary, the five-member heterocyclic compounds with nitrogen and sulfur or oxygen as the heteroatoms are weak one-electron reducing agents due to the weaker electron donating property of S and O atoms than N atom. Then with these compounds as n-type dopants, the ambipolar transporting property can be achieved with p-channel semiconductors by n-type doping usable for complex digital circuits applications. And with such alternative embodiments (e.g., Formula A) and the imidazole derivatives, a dopants library can be obtained with different tunable doping ability, which is very important for their applications in organic electronic devices, carbon nanotube and graphene devices.

Also according to the present disclosure, another alternative structure relates to the above structure of Formula A by replacing the Ns therein with B atoms, such as represented in the following Formula B:

Formula B

(corresponding to the structure:

to act as a p-type dopant with low-lying LUMO energy levels.

Based on the discussion for the alternative structure/embodiment discussed above in connection with Formula A, if the N atoms in imidazole derivatives are replaced by electron deficient atoms such as B atom (applied to control the band gap and improve the electron-transporting ability of organic semiconductors as related in Jakle F. *Chem. Rev.* 2010, 110, 3985), the dopants are obtained with strong electron-accepting property as a candidate of p-type dopants in organic semiconductors.

By Gaussian 03' calculation, the SOMO level of the neutral radical of 1,3-dimethyl-2-(perfluorophenyl)-2,3-dihydro-1H-benzo[d][1,3]diborole (DMBIB-5F, FIG. 2) is −5.85 eV, which is much lower than the LUMO level of the typical p-type dopant, F4-TCNQ (Leo K. *Chem. Rev.* 2007, 107, 1233), indicating its ability to act as a strong p-type dopant. The molecular structures of the five-member heterocyclic compounds with boron heteroatoms are as follows:

It should be appreciated that in connection with the structure represented by Formula A, for all R groups, reference herein to the aryl groups encompasses thiophenes and other aromatic rings; such as In connection with the structure represented by Formula A, it should also be appreciated that, for A and B groups, reference herein to sp3- and sp2-hybridized carbon atoms encompasses all such alkyl and aryl groups.

Various embodiments described above and shown in the figures may be implemented together and/or in other manners. One or more of the items depicted in the drawings/figures can also be implemented in a more separated or integrated manner, or removed and/or rendered as inoperable in certain cases, as is useful in accordance with particular applications. For example, embodiments involving the doping of organic semiconductors as discussed above may be implemented using different/additional dopants or solution materials, and with different types of substrates. As further examples consistent herewith, certain embodiments of the above-characterized devices implement the organic material with an n-type dopant material in a layer in contact with an organic semiconductor layer of the electronic device; the dopant material layer in the multilayer structure is in one instance below, and in another instance on, the organic semiconductor layer (e.g., as opposed to being on the organic semiconductor substrate). In view of the description herein, those skilled in the art will recognize that many changes may be made thereto without departing from the spirit and scope of the present invention.

What is claimed is:

1. A device, comprising:
   an organic material, including a carbon-nanotube or graphene structure;
   in a portion of the organic material, an n-type dopant material including an imidazole-based material including a hydrogen-based material bonded between nitrogen atoms; and
   wherein the n-type dopant material includes an imidazole-based material having the formula:

in which A and B include at least one of sp$^3$- and sp$^2$-hybridized carbon atoms, R1 includes at least one of an H atom, an alkyl group, an aryl alkyl group, an sp2-hybridized carbon atom bonded group and borane, R2 and R3 include at least one of an H atom and at least one sp3- or sp2-hybridized carbon atom bonded group and X includes an H atom, wherein the imidazole-based material is configured with at least one ring wherefrom each R group (R1, R2, R3) branches, with none of R1, R2, and R3 being chemically bonded with another of R1, R2, and R3.

2. The device of claim 1, wherein the imidazole-based material includes at least one sp$^3$- or sp$^2$-hybridized carbon atom bonded to the nitrogen atoms, and the n-type dopant material is the imidazole-based material.

3. The device of claim 1, wherein the hydrogen-based material is selected from the group of: a hydrogen atom, an alkyl group, and an aryl group, and the imidazole-based material includes benzoimidazole.

4. The device of claim 1, wherein the n-type dopant material is a precursor material configured to generate a dopant that dopes the organic material.

5. The device of claim 1, wherein the n-type dopant material is a precursor material blended with an organic matrix material and configured to generate a dopant that dopes the organic material.

6. The device of claim 1, wherein the imidazole-based material is blended with at least one organic matrix material in the organic material.

7. The device of claim 1, wherein the organic material having an n-type dopant material is in a layer in contact with an organic semiconductor layer of the device.

8. The device of claim 1, wherein the n-type dopant material is configured to dope the portion of the organic material via contact doping.

9. The device of claim 1, wherein the imidazole-based material is configured to increase the conductivity of the organic material.

10. The device of claim 1, wherein
the organic material traps electron charge carriers that decrease the mobility in the organic material in an ambient atmosphere, and
the imidazole-based material is configured to n-dope the organic material to increase the conductivity of the organic material to compensate for the decreased mobility due to the trapped electron charge carriers.

11. The device of claim 1, wherein
the organic material includes impurities that trap electron charge carriers that restrict the charge transport through the organic material, and
the imidazole-based material is configured to n-dope the organic material to increase the mobility in the organic material to compensate for the restricted charge transport.

12. The device of claim 1, wherein the imidazole-based material is configured to n-dope the organic material to mitigate conductivity changes due to oxidation of the organic material.

13. The device of claim 1, wherein the imidazole-based material is configured to facilitate hydrogen transfer and form radicals that n-dope the organic material.

14. The device of claim 1, wherein the n-type dopant material is a precursor material configured to generate active dopant radicals in response to at least one of thermal activation and photo-activation.

15. The device of claim 1, wherein the imidazole-based material is configured to form radicals by forming radicals with electrons in high-lying HOMOs in the dopant, and to dope the organic material with the radicals.

16. The device of claim 1, wherein the organic material includes an organic semiconductor material, and wherein the n-type dopant material is in the organic semiconductor material and increases the mobility of the organic semiconductor material, relative to undoped portions of the organic semiconductor material.

17. The device of claim 1, wherein the n-type dopant material comprises:
an imidazole-based material including a hydrogen-based material bonded between nitrogen atoms, the imidazole-based material configured to n-dope organic semiconductor materials, and characterized by a modification of the following formula, wherein the modification corresponds to replacement of Ns therein with B atoms, in which each of A and B includes at least one of $sp^3$- and $sp^2$-hybridized carbon atoms, R1 includes at least one of an H atom, an alkyl group, an aryl alkyl group, an sp2-hybridized carbon atom bonded group and borane, R2 and R3 include at least one of an H atom and at least one sp3- or sp2-hybridized carbon atom bonded group and X includes an H atom.

18. A device, comprising:
an organic material, including a carbon-nanotube or graphene structure; and
in a portion of the organic material, an n-type dopant material including an imidazole-based material including a hydrogen-based material bonded between nitrogen atoms, wherein the n-type dopant material includes an imidazole-based material having the formula:

in which A and B include at least one of $sp^3$- and $sp^2$-hybridized carbon atoms, R1 includes at least one of an H atom, an alkyl group, an aryl alkyl group, an sp2-hybridized carbon atom bonded group and borane, R2 and R3 include at least one of an H atom and at least one sp3- or sp2-hybridized carbon atom bonded group and X includes an H atom, wherein the imidazole-based material is configured with at least one ring wherefrom each R group (R1, R2, R3) branches, with none of R1, R2, and R3 being chemically bonded with another of R1, R2, and R3; and
wherein the Fermi level of the carbon nanotubes or the graphene structure is below −2.5 eV, and wherein the portion of the organic material including the n-type dopant is a channel region for at least one of an organic thin-film transistor, organic light-emitting diode, organic photovoltaic device, or organic electronic sensor.

19. A device, comprising:
an organic material, including a carbon-nanotube or graphene structure;
in a portion of the organic material, an n-type dopant material including an imidazole-based material including a hydrogen-based material bonded between nitrogen atoms;
wherein the n-type dopant material includes an imidazole-based material having the formula:

in which A and B include at least one of $sp^3$- and $sp^2$-hybridized carbon atoms, R1 includes at least one of an H atom, an alkyl group, an aryl alkyl group, an sp2-hybridized carbon atom bonded group and borane, R2 and R3 include at least one of an H atom and at least one sp3- or sp2-hybridized carbon atom bonded group and X includes an H atom, wherein the imidazole-based material is configured with at least one ring wherefrom each R group (R1, R2, R3)

branches, with none of R1, R2, and R3 being chemically bonded with another of R1, R2, and R3;
 a dielectric layer and an organic semiconductor substrate; and
 wherein the organic material having the n-type dopant material is in a layer between the dielectric layer and the organic semiconductor substrate.

20. A device, comprising: an organic material; and in a portion of the organic material, an n-type dopant material including an imidazole-based material including a hydrogen-based material bonded between nitrogen atoms, and wherein the imidazole-based material includes a derivative of 1,3-dimethyl-2-phenyl-2,3-dihydro-1H-benzoimidazole (DMBI) configured to dope the organic material via substitution.

21. The device of claim 20, wherein the organic material includes an organic semiconductor material, and wherein the n-type dopant material is in the organic semiconductor material and increases the mobility of the organic semiconductor material, relative to undoped portions of the organic semiconductor material.

22. A device, comprising: an organic material; and in a portion of the organic material, an n-type dopant material including an imidazole-based material including a hydrogen-based material bonded between nitrogen atoms, and wherein the imidazole-based material is selected from the group of: 1,3-dimethyl-2-phenyl-2,3-dihydro-1H-benzoimidazole; 2-(2,4-dichlorophenyl)-1,3-dimethyl-2,3-dihydro-1H-benzoimidazole (C1-DMBI); (4-(1,3-dimethyl-2,3-dihydro-1H-benzoimidazole-2-yl)-phenyl)-dimethyl-amine (N-DMBI); and 2-(1,3-dimethyl-2,3-dihydro-1H-benzoimidazol-2-yl)-phenol (OH-DMBI).

23. The device of claim 22, wherein the organic material includes an organic semiconductor material, and wherein the n-type dopant material is in the organic semiconductor material and increases the mobility of the organic semiconductor material, relative to undoped portions of the organic semiconductor material.

24. An organic-material device comprising:
 a substrate;
 a gate electrode;
 a gate oxide on the gate electrode;
 an organic semiconductor material over the gate oxide;
 a passivation layer including BCB (divinyltetramethyldisiloxane bis(benzocyclobutene)) on the gate oxide and between the gate oxide and the organic semiconductor material, the passivation layer configured to mitigate oxidation at an interface region between the gate oxide and the organic semiconductor material;
 source and drain electrodes; and
 in a portion of the organic material, a channel region being configured to electrically couple the source and drain electrodes and having
  a surface region having impurities that trap electron charge carriers and mitigate charge transport between the source and drain electrodes, and
  an n-type dopant material including an imidazole-based material with a hydrogen-based material bonded between nitrogen atoms, the n-type dopant material being configured to increase the mobility of the organic material to compensate for decreased mobility due to the trapped electron charge carriers, wherein the n-type dopant material includes an imidazole-based material having the formula:

in which A and B include at least one of sp$^3$- and sp$^2$-hybridized carbon atoms, R1 includes at least one of an H atom, an alkyl group, an aryl alkyl group, an sp2-hybridized carbon atom bonded group and borane, R2 and R3 include at least one of an H atom and at least one sp3- or sp2-hybridized carbon atom bonded group and X includes an H atom, wherein the imidazole-based material is configured with at least one ring wherefrom each R group (R1, R2, R3) branches, with none of R1, R2, and R3 being chemically bonded with another of R1, R2, and R3.

25. The organic-material device of claim 24, wherein the n-type dopant is doped in an organic matrix material.

26. The organic-material device of claim 25, wherein the n-type dopant is chemically grafted onto a dielectric material, and the organic matrix material is over or on the chemically grafted n-type dopant.

27. The organic-material device of claim 25, wherein the n-type dopant is mixed with the organic matrix material and the mixture is over or on the substrate.

28. The organic-material device of claim 25, wherein the n-type dopant is patterned on the organic matrix material with selectively doped portions of the organic device at the patterned regions of the n-type dopant.

29. The organic-material device of claim 25, wherein the organic matrix material includes radicals with the n-type dopant and the organic matrix material is doped with the radicals.

30. An organic thin-film device at an intermediate stage of manufacture, the device comprising:
 a substrate; and
  on the substrate, a solution or a vapor including an n-type dopant having an imidazole-based material therein mixed or in contact with an organic matrix material, the imidazole-based material including a hydrogen-based material bonded between nitrogen atoms, the solution configured to form an organic charge transport layer doped with a dopant from the imidazole-based material, wherein the n-type dopant material includes an imidazole-based material having the formula:

in which A and B include at least one of sp$^3$- and sp$^2$-hybridized carbon atoms, R1 includes at least one of an H atom an alkyl group, an aryl group, an sp2-hybridized carbon atom bonded group and borane, R2 and R3 include at least one of an H atom and at least one sp3- or sp2-hybridized carbon atom bonded group and X includes an H atom, wherein the imidazole-based material is configured with at least one ring wherefrom each R group (R1, R2, R3) branches, with none of R1, R2, and R3 being chemically bonded with another of R1, R2, and R3.

* * * * *

UNITED STATES PATENT AND TRADEMARK OFFICE
CERTIFICATE OF CORRECTION

PATENT NO. : 9,133,130 B2
APPLICATION NO. : 13/080564
DATED : September 15, 2015
INVENTOR(S) : Wei et al.

Page 1 of 1

It is certified that error appears in the above-identified patent and that said Letters Patent is hereby corrected as shown below:

<u>In the Specification</u>

Col. 12, line 67: delete "aromatic rings; such as" and insert --aromatic rings;--.

<u>In the Claims</u>

Col. 18, line 63, Claim 30: delete "H atom an alkyl group, an aryl group, an" and insert --H atom, an alkyl group, an aryl alkyl group, an--.

Signed and Sealed this
Second Day of August, 2016

Michelle K. Lee
*Director of the United States Patent and Trademark Office*